(12) United States Patent
Gerner et al.

(10) Patent No.: US 6,675,835 B2
(45) Date of Patent: Jan. 13, 2004

(54) ELLIPTICAL TUBING IN DEGASSING AND PULSATION DAMPENER APPLICATION

(75) Inventors: Yuri Gerner, Mendota Heights, MN (US); Carl W. Sims, St. Paul, MN (US); Thomas Thielen, Plymouth, MN (US)

(73) Assignee: Systec, Inc., New Brighton, MN (US)

( * ) Notice: Subject to any disclaimer, the term of this patent is extended or adjusted under 35 U.S.C. 154(b) by 187 days.

(21) Appl. No.: 09/901,824

(22) Filed: Jul. 10, 2001

(65) Prior Publication Data

US 2003/0041911 A1 Mar. 6, 2003

(51) Int. Cl.⁷ .............................................. F16L 55/04
(52) U.S. Cl. .................... 138/30; 138/26; 138/DIG. 11; 95/46; 96/6; 96/10
(58) Field of Search ..................... 138/30, 28, DIG. 11; 95/46; 96/6, 8, 10

(56) References Cited

U.S. PATENT DOCUMENTS

| | | | | |
|---|---|---|---|---|
| 2,212,281 A | | 8/1940 | Ullstrand | |
| 2,315,179 A | | 3/1943 | Allender | |
| 2,407,276 A | * | 9/1946 | Hendel et al. | 138/26 |
| 3,348,578 A | * | 10/1967 | Mercier | 138/30 |
| 3,742,727 A | | 7/1973 | Kaiser | |
| 3,782,418 A | | 1/1974 | Zahid | |
| 4,064,911 A | | 12/1977 | Albrecht | |
| 4,088,154 A | * | 5/1978 | Patton et al. | 138/30 |
| 4,234,427 A | | 11/1980 | Boehme | |
| 4,281,687 A | | 8/1981 | Hutchins et al. | |
| 4,299,253 A | * | 11/1981 | Burton | 138/30 |
| 4,325,715 A | * | 4/1982 | Bowman et al. | 55/158 |
| 4,523,612 A | * | 6/1985 | Kuklo | 138/30 |
| 4,548,240 A | | 10/1985 | Graham | |
| 4,548,713 A | | 10/1985 | Schmid | |
| 4,552,182 A | | 11/1985 | Graham | |
| 4,729,773 A | * | 3/1988 | Shirato et al. | 55/158 |
| 4,986,837 A | * | 1/1991 | Shibata | 55/190 |
| 5,111,848 A | | 5/1992 | Inukai | |
| 5,425,803 A | * | 6/1995 | Van Schravendijk et al. | 95/46 |
| 5,762,684 A | * | 6/1998 | Hayashi et al. | 95/24 |
| 5,862,832 A | | 1/1999 | Victor et al. | |
| 6,029,711 A | * | 2/2000 | Koch et al. | 138/118 |
| 6,039,078 A | | 3/2000 | Tamari | |
| 6,063,275 A | | 5/2000 | Traylor | |
| 6,076,557 A | | 6/2000 | Carney | |
| 6,085,796 A | | 7/2000 | Riga | |
| 6,123,108 A | | 9/2000 | Chen et al. | |
| 6,248,157 B1 | * | 6/2001 | Sims et al. | 96/6 |
| 6,305,421 B1 | * | 10/2001 | Ahrweiler | 138/30 |
| 6,309,444 B1 | * | 10/2001 | Sims et al. | 95/46 |
| 6,494,938 B2 | * | 12/2002 | Sims et al. | 96/6 |

\* cited by examiner

*Primary Examiner*—James Hook

(57) ABSTRACT

A flow-dampening degassing apparatus for transport of liquid chromatography fluids therethrough includes a substantially burdoin-shaped flexible tube disposed in a reduced-pressure chamber, the tube being sufficiently flexible to expand in a cross-sectional direction upon incursion of a fluid pulsation to thereby increase an inner volume of the tube and correspondingly reduce fluid pressure therein. In a particular embodiment, the tube is fabricated from a gas-permeable and liquid-impermeable material for degassing transported fluids in the reduced-pressure chamber.

8 Claims, 3 Drawing Sheets

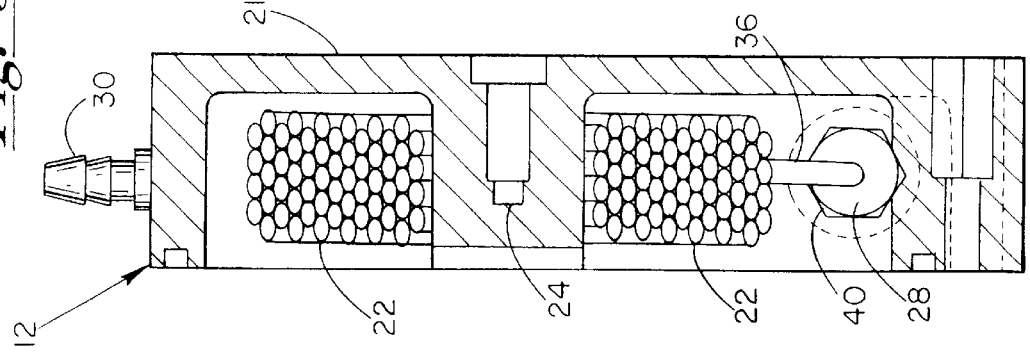
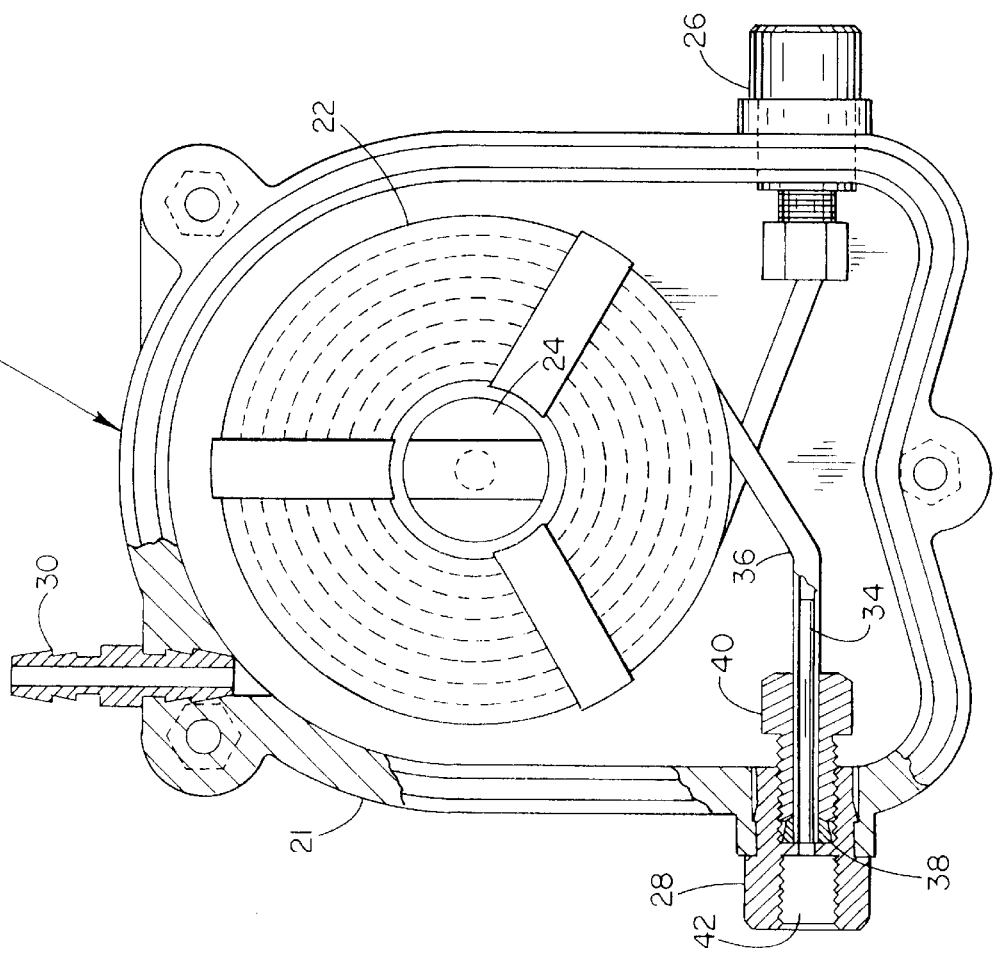

ELLIPTICAL TUBING IN DEGASSING AND PULSATION DAMPENER APPLICATION

FIELD OF THE INVENTION

The present invention relates to vacuum degassing and pulse-dampening systems generally, and more particularly to vacuum degassing, pulse-dampening systems for use in liquid chromatography applications. This invention also relates to methods for dampening flow pulsations and degassing mobile phase materials.

BACKGROUND OF THE INVENTION

A variety of applications exist today involving the use of fluid solvents or reactants, wherein the presence of dissolved gases, particularly air, is undesirable. One example of such an application relates to mobile phases in high performance liquid chromatography, where the presence of even small amounts of dissolved gases can interfere with the accuracy and sensitivity of the results obtained. In some cases, the dissolved gases can form bubbles in the mobile phase, thereby causing measurement error in chromatographic applications. Furthermore, some dissolved gases can cause deleterious effects on the mobile phase as well as the surrounding componentry. Often times, such detrimental effects caused by the dissolved gases is related to the relative concentration of the gases in the mobile phase. To avoid such effects, the gases are typically removed from the mobile phase through a known degassing process.

An additional issue that exists in present liquid chromatography systems involves the necessity of dampening fluid pressure pulsations flowing through respective flow conduits and through respective chromatographic columns, which pulsations result from uneven draw and discharge from positive-displacement fluid pumps, such as reciprocating pumps. To obtain the most accurate chromatographic measurements possible, fluid (mobile phase) flow through the column and the detector should be nearly constant. Thus, in order to obtain a continuous fluid flow at a substantially constant rate, it is desirable to provide the chromatographic system with a pulse-dampener in the fluid flow conduit between the fluid pump and the column/detector.

Fluid pressure pulsations in liquid chromatography systems may also occur upstream from respective fluid pumps, thereby adversely affecting chromatographic operations upstream from the fluid pump. In many applications, the mobile phase transported through the liquid chromatography system is a blend of multiple solvents. In such embodiments, individual solvent reservoirs are operably connected to a blending valve apparatus to blend desired quantities of the distinct solvents into a unitary mobile phase. Solvent may be drawn from the respective reservoirs into the blending valve apparatus by a downstream fluid pump, which pump subsequently delivers the blended mobile phase to the remaining chromatographic components. Because of the pulsation characteristics of the fluid pump, it is desirable to provide mechanisms for dampening such pulsations between the respective solvent reservoirs and the blending valve apparatus, as well as downstream from the blending valve apparatus. Fluid flow pulsations drawn into the blending valve apparatus have the tendency to decrease the accuracy of the blended mobile phase, such that desired ratios of respective solvents comprising the blend may not be accurate. Further, fluid flow pulsations into the blending apparatus can negatively effect physical componentry in the blending valve apparatus, and may decrease the overall life expectancy thereof. It is therefore desirable to provide a pulse-dampening characteristic to the fluid flow conduits connecting such chromatographic components, and particularly between respective fluid reservoirs and a mobile phase blending apparatus.

A number of pulse-dampening techniques have been implemented to provide such flow-dampening characteristics in liquid chromatography applications. For example, fluid has been routed into expandable chambers, wherein a sudden influx of fluid pressure causes the expandable chamber to correspondingly expand, thereby increasing internal volume and absorbing excess fluid pressure to maintain a relatively constant fluid pressure downstream of the expandable chamber. Such flow-dampening devices, however, can result in non-laminar flow patterns, which may result in detrimental formation of gas bubbles in the bulk of the mobile phase. As described above, such gas bubbles can interfere with accurate chromatographic analysis.

Other proposed systems provide dead volumes in the fluid flow pathways, which volumes are not completely filled in standard flow regimes. Upon fluid flow pulsations, however, the dead volumes accumulate the excess fluid flow, thereby mitigating the flow impact downstream of the dead volumes. As with the expandable chambers, however, the dead volumes may act to promote non-laminar flow in the fluid conduits.

Some applications utilize elliptical or flattened tubes as pulse-dampening fluid conduits. Such pulse-dampening tubes are sufficiently flexible to change in cross-sectional profile when a fluid pulse is directed through the tubes. Typical such applications, however, surround the flexible tubing with restraining means for limiting the extent of cross-sectional distention. Such restraining means act against change in cross-sectional profile of the fluid conduits so that the fluid conduits return to an elliptical or flattened profile after the fluid pulse has been dampened. Such restraining means include biasing means, external bodies, and compressible fluids surrounding the fluid conduits.

In addition, the flow-dampening systems proposed to date fail to address the degassing issue in liquid chromatography applications as described above. A particular method of degassing mobile phases includes the use of semi-permeable synthetic polymer resin materials as a fluid conduit material, and the exposure of such a semi-permeable conduit to a reduced pressure or vacuum environment. To perform the degassing, the fluid to be degassed is caused to flow through the conduit in the reduced pressure environment, which allows the dissolved gases to escape from the mobile phase through the semi-permeable conduit walls. By addressing both the degassing functions and the flow-dampening functions in a single apparatus, increased chromatographic efficiency and reduced-sized chromatographic instruments may be achieved.

Accordingly, it is a principle object of the present invention to provide a means for simultaneously degassing a mobile phase and dampening pulsations in such a mobile phase using one or more semi-permeable tubes.

A further object of the present invention is to provide a fluid pulse-dampening apparatus having degassing capabilities.

A still further object of the present invention is to provide a substantially elliptical-shaped flexible tube for dampening flow pulsations and for degassing fluids passing therethrough.

A yet further object of the present invention is to provide a substantially elliptical-shaped flexible tube in a reduced-pressure chamber for degassing fluids passing through the tube, which tube further acts to dampen fluid pulsations passing therethrough.

Another object of the present invention is to provide a flow-dampening degassing apparatus capable of withstanding fluid pulsations of up to about 100 pounds per square inch.

A still further object of the present invention is to provide a fluid pulse-dampening apparatus having fluid degassing capabilities, wherein the apparatus is substantially configured to maintain laminar fluid flow therewithin.

SUMMARY OF THE INVENTION

By means of the present invention, an apparatus for simultaneously dampening fluid flow pulsations and degassing fluids passing through a semi-permeable tube is provided. This is achieved by forming the tube in a substantially elliptical-shaped configuration, with the tube being fabricated from a gas-permeable and liquid-impermeable material such as an amorphous perfluorinated copolymer. Through the use of such amorphous perfluorinated copolymers, tubes having sufficient flexibility to extend in a cross-sectional direction for fluid flow pulse-dampening characteristics may be fabricated without compromising fluid degassing characteristics. Through such an apparatus, design efficiency of liquid chromatography applications is enhanced by combining flow-dampening and degassing functionality into one apparatus, as described in the present application.

One embodiment of the flow-dampening degassing apparatus of the present invention includes a substantially elliptical-shaped flexible tube disposed in a chamber, which chamber is preferably operably coupled to a vacuum source such that the chamber has a reduced internal pressure. The tube is preferably sufficiently flexible to expand in a cross-sectional direction upon incursion of a fluid pulsation to thereby increase an inner volume and correspondingly reduce fluid pressure therein, while also being sufficiently resilient to return to its original configuration after the pulse has been dampened. The tube is operably coupled to a fluid pump, which pump may render fluid flow pulsations both upstream and downstream therefrom. The tube is preferably a gas-permeable and liquid-impermeable material, and is more preferably an amorphous perfluorinated copolymer such as TEFLON AF∞. The tube preferably has a wall thickness of between about 0.002 inches and about 0.010 inches, such that the tube can effectively dampen fluid pulsations of up to about 100 pounds per square inch. Such an embodiment of the flow-dampening degassing apparatus is preferably utilized in conjunction with a high performance liquid chromatography system.

BRIEF DESCRIPTION OF THE DRAWINGS

FIG. 2 is a cross-sectional view of the flow-dampening degassing apparatus illustrated in FIG. 1.

FIG. 3 is a cut-away cross-sectional side view of the flow-dampening degassing apparatus illustrated in FIG. 2.

DETAILED DESCRIPTION OF THE PREFERRED EMBODIMENTS

The objects and advantages enumerated above together with other objects, features and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
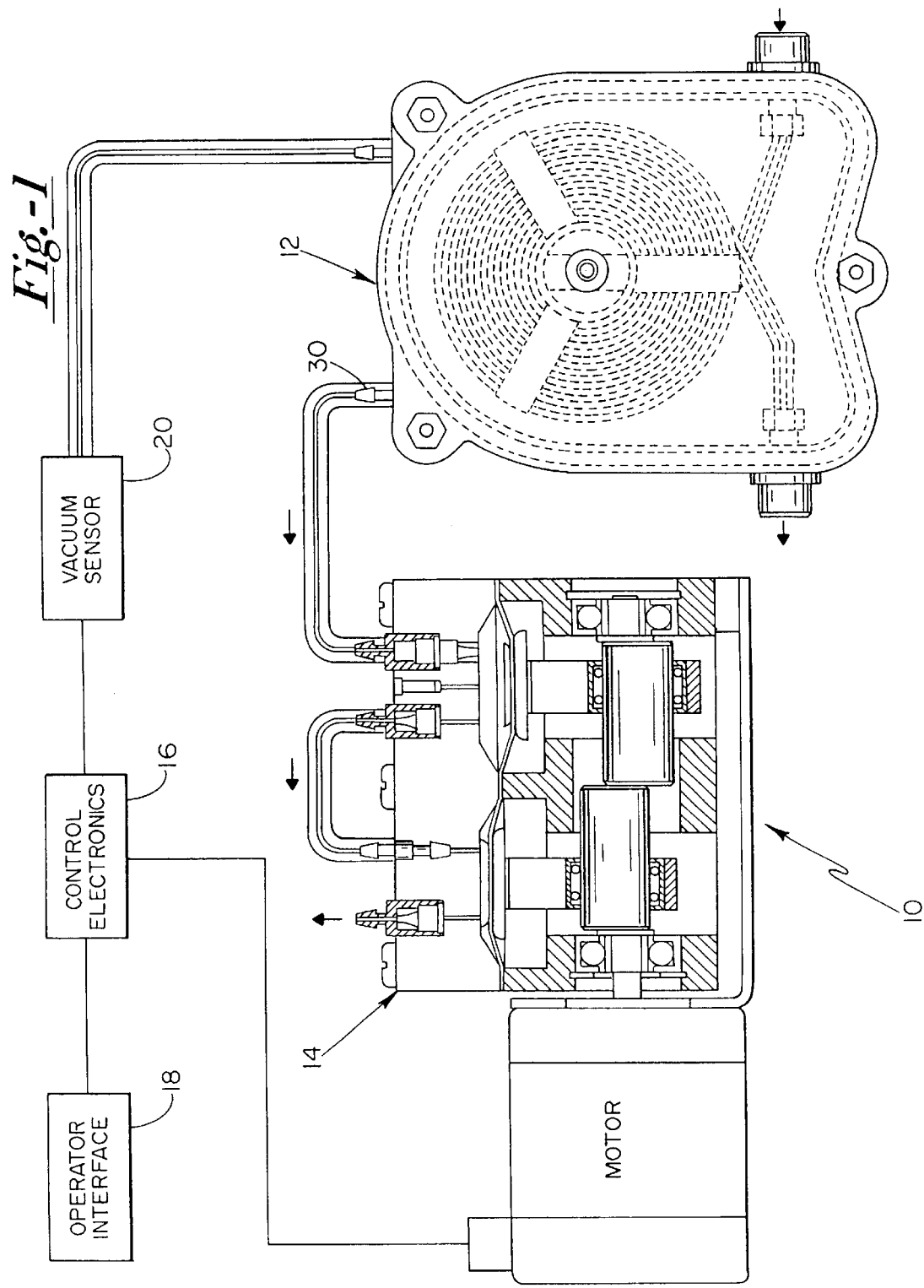
FIG. 1 is a schematic diagram showing a flow-dampening degassing apparatus of the present invention.

Referring now by characters of reference to the drawings and first to FIG. 1, a flow-dampening degassing system 10 is shown. Flow-dampening degassing system 10 preferably includes a vacuum chamber 12 which is operably coupled to a vacuum pump 14, which pump 14 serves as a vacuum source to reduce internal pressure within vacuum chamber 12. In the embodiment shown in FIG. 1, flow-dampening degassing system 10 further includes a vacuum sensor 20 operably coupled to vacuum chamber 12, and electronic control means 16 operably coupled to vacuum pump 14 and to vacuum sensor 20, and an operator interface 18 operably coupled to control means 16.

Vacuum chamber 12 may be embodied in a variety of configurations, and is illustrated in FIG. 1 as a representative embodiment of such vacuum chambers. As can be seen more clearly in FIG. 2, vacuum chamber 12 is preferably manufactured from a high-impact polymer material, such as high density polyethylene or polypropylene, which can be readily assembled with sealing o-rings or heat welded together to form a strong, relatively inert, non-metallic housing 21. As shown in FIG. 2, a flow-dampening degassing tube 22 may be wound about a central shaft or spool member 24 to form a coil. In such a manner, a relatively large amount of flow-dampening degassing tube 22 is exposed to the reduced pressure environment within vacuum chamber 12, thereby providing an efficient means for degassing and pulse-dampening fluids passing through tube 22. Flow-dampening degassing tube 22 preferably extends between an inlet connection 26 and an outlet connection 28. Vacuum chamber 12 preferably further includes a vacuum connection 30 for connection to a vacuum source, preferably vacuum pump 14.

Flow-dampening degassing tube 22 is preferably a semi-permeable polymeric material. In preferred embodiments, flow-dampening degassing tube 22 is a gas-permeable and liquid-impermeable material such as an amorphous perfluorinated copolymer. An example of such an amorphous perfluorinated copolymer is TEFLON AF™ 2400 manufactured by E. I. du Pont de Nemours and Company. TEFLON AF™ is a preferred material for use in flow-dampening degassing tube 22 for its desirable degassing and inertness characteristics. TEFLON AF™, when manufactured to desired wall thicknesses, is also sufficiently flexible to perform the flow-dampening functions described herein.

Inlet and outlet connections 26, 28 preferably include a short length of interface tubing 34 which may be high strength, high density, relatively inert material, such as PEEK or, if metal, titanium or stainless steel, and having an end as at 36 over which flow-dampening degassing tube 22 is fitted. In preferred embodiments, interface tube 34 may be connected using an appropriate sealing ferrule 38 which may be TEFZEL or other high impact inert material used in conjunction with a nut 40 to connect interface tube 34 to bulkhead union 42.

As is shown in the cut-away side view of FIG. 1, flow-dampening degassing tube 22 is substantially elliptical-shaped, thereby being larger in a first cross-sectional dimension than in a second cross-sectional dimension. Such a preferred configuration of flow-dampening degassing tube 22 allows tube 22 to expand in a direction along the second cross-sectional dimension, thereby increasing the internal volume of tube 22 upon incursion of a fluid pulsation. By increasing the internal volume within tube 22, internal fluid pressure is correspondingly decreased, and the fluid pulsation thereby dampened. Once the fluid pulsation has been dampened, resiliency in tube 22 causes the tube to regain its original, substantially elliptical-shaped configuration. Flow-dampening degassing tube 22 preferably has a wall thickness of between about 0.002 inches and about 0.010 inches, though a variety of tube wall thicknesses may be employed to handle various expected internal fluid pressures and fluid pulsations. In preferred embodiments, however, tube 22 is capable of handling and dampening flow pulsations of up to about 100 pounds per square inch. If greater wall thicknesses are utilized in tube 22, however, larger fluid pulsation pressures may be effectively dampened.

In some embodiments, inlet connection 26 is downstream from a fluid pump (not shown) whereby vacuum chamber 12 is preferably disposed between a fluid pump and downstream components, which components are operably coupled to outlet connection 28. In a particularly preferred embodiment, vacuum chamber 12 is utilized in conjunction with a high-performance liquid chromatography system, wherein a mobile phase is pumped through flow-dampening degassing tube 22 in vacuum chamber 12, and into a chromatographic column for analysis of such mobile phase.

Figure 4:
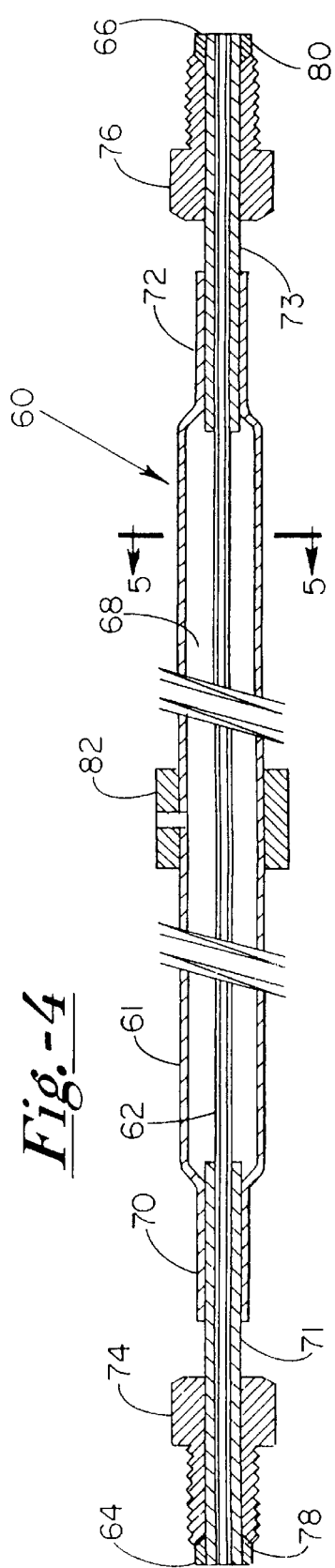
FIG. 4 is a cross-sectional view of an alternative embodiment of a flow-dampening degassing apparatus of the present invention.

Another embodiment of the present invention is illustrated in FIG. 4, wherein an in-line vacuum chamber 61 is shown. Flow-dampening degassing system 60 includes a flow-dampening degassing tube 62, which is preferably disposed between various liquid chromatography system components, including those upstream from said pump. Flow-dampening degassing tube 62 preferably extends between opposite ends 64 and 66, and is disposed in interior portion 68 of vacuum chamber 61.

Vacuum chamber 61 is preferably PEEK, but may be any high strength, relatively inert material. Vacuum chamber 61 may be sealed at ends 70 and 72 through the use of PTFE/FEP dual-shrink tubing 71, 73 which is disposed in surrounding relationship to tube 62. Preferably, a pair of nuts 74, 76 in conjunction with a pair of ferrules 78, 80 are formed in surrounding relationship to tubing 71, 73 for connecting vacuum chamber 61 between respective liquid chromatography system components. As shown in FIG. 4, a vacuum adapter 82 is provided for communication between interior portion 68 of vacuum chamber 61 and a vacuum source (not shown) to evacuate interior portion 68.

Figure 5:
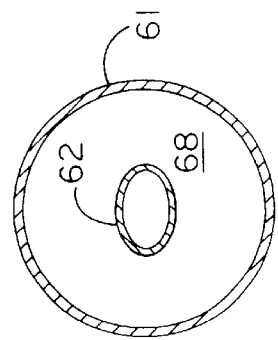
FIG. 5 is a cut-away cross-sectional end view taken along cut line 5 of FIG. 4.

FIG. 5 is a cross-sectional end view taken along line 5 shown in FIG. 4. As illustrated in FIG. 5, flow-dampening degassing tube 62 is preferably substantially elliptical-shaped such that a first cross-sectional dimension is larger than a second cross-sectional dimension. As described herein, such a preferred configuration provides desired flow-dampening characteristics.

The flow-dampening degassing tube of the present invention preferably simultaneously acts to degas fluids flowing therethrough and to dampen fluid flow pulsations. In preferred embodiments, the flow-dampening degassing tube is disposed in a reduced-pressure vacuum chamber to provide desired degassing functionality. In such a manner, the distinct functions of degassing and flow-dampening, which are important to liquid chromatography applications, may be combined in a single apparatus as in the present invention. By combining such functions, liquid chromatography systems may be fabricated in a more compact and efficient manner.

In use, the flow-dampening degassing apparatus of the present invention degasses fluids passing therethrough and dampens fluid pressure pulsations incurred therein. The flow-dampening degassing tube preferably conducts fluid driven by a fluid pump, which pump may be positive displacement type fluid pump. Thus, the flow-dampening degassing tube may be operably coupled to the fluid pump inlet or outlet, or may be disposed remotely from the pump. In particular, the tube of the present invention is preferably utilized between respective solvent reservoirs and a blending valve apparatus, as well as between the blending valve apparatus and downstream chromatographic components.

In many of such pumps, fluid flow deviations occur on a semi-regular basis. Therefore, fluid flow pulsations are quite typical in such applications. To enhance measurement accuracy in liquid chromatography applications, the flow-dampening degassing tube is preferably temporarily expandable in a cross-sectional direction to increase the volume within the tube, and thereby decrease fluid pressure therein. In practice, the fluid pulsation causes the flow-dampening degassing tube to momentarily expand, which acts to dampen such a fluid flow pulse. Once the pulse has been dampened, residual resilient forces in the flow-dampening degassing tube act to reconfigure the tube in a substantially elliptical-shaped configuration, thereby readying the tube for a subsequent fluid flow pulsation. The net effect of such dampening is to normalize the fluid flow exiting the flow-dampening degassing apparatus so that chromatographic instruments downstream of the flow-dampening degassing apparatus receive a relatively constant flow rate of fluid.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A flow-dampening degassing apparatus for transport of liquid chromatography fluids therethrough, said flow-dampening degassing apparatus comprising:

a substantially elliptical-shaped flexible tube disposed in a chamber, said chamber being operably coupled to a vacuum source such that said chamber has a reduced internal pressure, said tube being sufficiently flexible to expand in a cross-sectional direction upon incursion of a fluid pulsation to thereby increase an inner volume of said tube and correspondingly reduce fluid pressure therein, said tube comprising a gas-permeable and liquid-impermeable material.

2. A flow-dampening degassing apparatus as in claim 1 wherein said tube comprises an amorphous perfluorinated copolymer.

3. A flow-dampening degassing apparatus as in claim 1 wherein said tube has a wall thickness of between about 0.002 inches and about 0.010 inches.

4. A flow-dampening degassing apparatus as in claim 3 wherein said tube effectively dampens fluid pulsations of up to about 100 pounds per square inch.

5. A flow-dampening degassing apparatus as in claim 1 wherein said tube is operably coupled to a fluid pump outlet.

6. A flow-dampening degassing apparatus as in claim 1 wherein the fluid is a mobile phase used in high performance liquid chromatography applications.

7. A flow-dampening degassing apparatus as in claim 1 wherein said tube is sufficiently resilient to return to the substantially elliptical-shaped configuration after the fluid pulsation has been dampened.

8. A flow-dampening degassing apparatus as in claim 1 wherein said tube is operably disposed between one or more fluid reservoirs and a blending valve apparatus.

\* \* \* \* \*